United States Patent
Goodchild et al.

(10) Patent No.: US 9,757,391 B2
(45) Date of Patent: Sep. 12, 2017

(54) NEUROACTIVE STEROIDS AND THEIR USE TO FACILITATE NEUROPROTECTION

(71) Applicant: GOODCHILD INVESTMENTS PTY LTD, Malvern (AU)

(72) Inventors: Juliet M. Goodchild, Melbourne (AU); Colin S. Goodchild, Melbourne (AU)

(73) Assignee: GOODCHILD INVESTMENTS PTY LTD, Malvern, Victoria (AU)

( * ) Notice: Subject to any disclaimer, the term of this patent is extended or adjusted under 35 U.S.C. 154(b) by 262 days.

(21) Appl. No.: 14/440,617

(22) PCT Filed: Nov. 6, 2013

(86) PCT No.: PCT/AU2013/001283
§ 371 (c)(1),
(2) Date: May 5, 2015

(87) PCT Pub. No.: WO2014/071449
PCT Pub. Date: May 15, 2014

(65) Prior Publication Data
US 2015/0265632 A1  Sep. 24, 2015

Related U.S. Application Data

(60) Provisional application No. 61/724,492, filed on Nov. 9, 2012.

(51) Int. Cl.
| | | |
|---|---|---|
| A61K 31/57 | (2006.01) | |
| A61K 31/56 | (2006.01) | |
| A61K 31/573 | (2006.01) | |
| A61K 45/06 | (2006.01) | |
| A61K 9/00 | (2006.01) | |

(52) U.S. Cl.
CPC .......... *A61K 31/573* (2013.01); *A61K 31/56* (2013.01); *A61K 31/57* (2013.01); *A61K 45/06* (2013.01); *A61K 9/0019* (2013.01)

(58) Field of Classification Search
None
See application file for complete search history.

(56) References Cited

U.S. PATENT DOCUMENTS

2012/0071453 A1  3/2012  Chodounska et al.

FOREIGN PATENT DOCUMENTS

| WO | 2006037016 A2 | 4/2006 |
| WO | 2011088503 A1 | 7/2011 |
| WO | 2013112605 | 8/2013 |

OTHER PUBLICATIONS

Bengtsson, et al., "Long-term Continuous Allopregnanolone Elevation Causes Memory Decline and Hippocampus Shrinkage in Female Wild-Type B6 Mice", Hormones and Behavior., vol. 78, Oct. 21, 2015, 8 pages.
Cervantes et al., "Brain Injury Following Cardiorespiratory Arrest in Cats. Effects of Alphaxalone-Alphadolon", Boletin De Estudios Medicos Y Biologicos, Universidad Nacional Autonoma De Mexico, vol. 37, No. 1/02, Jan. 1, 1989, 11 pages.
Chen, et al., "Allopregnanolone Promotes Regeneration and Reduces β-Amyloid Burden in a Preclinical Model of Alzheimer's Disease", Plos One, vol. 6, No. 8, Aug. 2011, 13 pages.
European Patent Application No. EP13853492.0, European Search Report, dated Jul. 13, 2016, 15 pages.
Goodchild, et al., "Prevention and Reversal of Morphine Tolerance by the Analgesic Neuroactive Steroid Alphadolone", Pain Medicine, vol. 10, No. 5, Jul. 1, 2009, 12 pages.
Yawno, et al., "Role of Neurosteroids in Regulating Cell Death and Proliferation in the Late Gestation Fetal Brain", Neuroscience. New York. NY. US, vol. 163, No. 3, Oct. 20, 2009, 10 pages.
International Application No. PCT/AU2013/001283, "International Search Report" dated Nov. 29, 2013.

*Primary Examiner* — Michael Barker
(74) *Attorney, Agent, or Firm* — Kilpatrick Townsend & Stockton LLP (57) ABSTRACT

The present disclosure teaches generally neuroprotection and in particular the use of non-hormonal neuroactive steroids to ameliorate inflammation of the central nervous system (CNS). More specifically, the present claims define methods of treating inflammation or ameliorating a neuroinflammatory-promoting condition in the CNS by administration of a steroid with certain properties formulated in a sulfobutyl ether beta-cyclodextrin composition. The steroid is neuroactive, devoid of hormonal endocrine activity and activates a pregnane X receptor. Examples of such steroids include alphaxalone, alphadolone allopregnanolone, pregnanolone, ganaxolone, hydroxydione, minaxolone, Org20599, Org21465, CT1341 and compounds of Formula (I). Dependent claims further define the type of the neuroinflammatory-promoting conditions, the type of cyclodextrin, the molar ratio of neuroactive steroid to the cyclodextrin and the inclusion of other active agents or excipients in the composition and their nature.

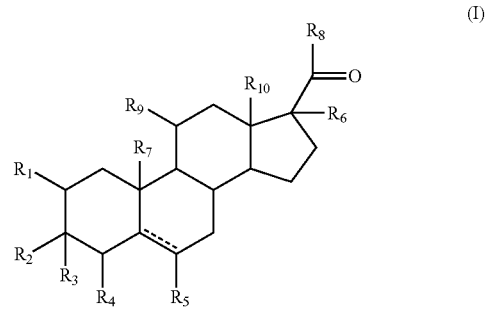

15 Claims, 4 Drawing Sheets

CRITICAL CARE PATIENTS

REACTIVE OXYGEN SPECIES
LIPOPOLYSACCHARIDE/INFECTION
STRESS/SURGERY
CHRONIC PAIN
LONG TERM OPIOID TREATMENT
CYTOTOXIC DRUGS
IRRADIATION glial activation in CNS
IL-1β   IL-6   TNFα

ANAESTHETICS

ALZHEIMER's
AMYLOID β

JNK/p38 MAP kinase activation

Neuroactive steroids stop complement activation

CEREBRAL ISCHAEMIA/STROKE
TRAUMATIC BRAIN INJURY
STRESS/TRAUMA
NEURODEGENERATIVE DISEASE
MULTIPLE SCLEROSIS

C3/5 activation

COGNITIVE IMPAIRMENT
? PERMANENT

CELL DEATH

NEUROACTIVE STEROIDS AND THEIR USE TO FACILITATE NEUROPROTECTION

PRIOR RELATED APPLICATIONS

This application is a National Phase application of International Application No. PCT/AU2013/001283, filed Nov. 6, 2013, which claims priority to U.S. Provisional Application No. 61/724,492, filed Nov. 9, 2012, each of which is incorporated herein by reference in its entirety.

FILING DATA

This application is associated with and claims priority from U.S. Provisional Patent Application No. 61/724,492, filed on 9 Nov. 2012, entitled "Neuroactive steroids and their use to facilitate neuroprotection", the entire contents of which, are incorporated herein by reference.

FIELD

The present disclosure teaches generally neuroprotection and in particular the use of non-hormonal neuroactive steroids to ameliorate inflammation of the central nervous system.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

It has become increasingly apparent that various neurological assaults to the central nervous system (CNS) can result in long lasting disturbances and neuronal dysfunction. These include the induction of a state of neuroinflammation leading to cognitive impairment, apoptosis of immature oligodendrocytes, alterations in synaptic architecture and decreased neurogenesis amongst other events (Briner et al. (2010) *Anesthesiolgy* 112:546-556; Tan et al. (2009) *Chin. Med J. (Engl)* 122:455-459; Zhu et al. (2010) *J. Cereb. Blood Flow Metabl* 30.1017-1030; Sanders et al. (2009) *Anesthesiology* 110:1077-1085).

The neurological assaults include the use of conventional anesthetics to induce anesthesia and sedation, chronic pain, infection, development of neurodegenerative conditions such as Alzheimer's disease and brain hypoxia and asphyxia. These and other conditions lead to neuroinflammation which can result in a spectrum of neurological damage.

Hence, there is concern about the potential toxic side effects of currently used anesthetic and sedative drugs and the vulnerability of the CNS to neurodegenerative processes resulting from infection and disease development. The brain has innate protective mechanisms against toxic xenobiotic substances (Selye (1971) *J Pharm Sci* 60: 1-28). One such mechanism involves a nuclear receptor, steroid and xenobiotic receptor (SXR) which regulates expression of catabolic enzymes in response to steroid and xenobiotic compounds (see U.S. Pat. No. 6,911,537). SXR is also known as pregnane X receptor (PXR).

However, these innate protective mechanisms may be less efficient in the very young, elderly or subjects under stress such as following an acute illness, infection, chronic pain or surgery (Ek et al. (2010) *Toxicol Lett* 197:61-59). Brinton (US Publication No. 2010/0105646) has contemplated the use of hormonal neuroactive steroid molecules such as allopregnanolone for neuroprotection. However, these molecules were not contemplated for use in treating inflammation nor required PXR activation. The molecules exhibit hormonal properties and induce sedative effects.

There is a need to develop neuroprotection protocols for use in relieving, ameliorating, reducing or otherwise decreasing neuroinflammation and neuroinflammatory-promoting conditions such as neurological assault.

SUMMARY

The present disclosure teaches the use of neuroactive non-hormonal steroids to induce neuroprotection of the central nervous system (CNS). The neuroactive steroids facilitate neuroprotection when either given in an anesthetic or sedating formulation or as a non-sedating neuroprotectant formulation. By "neuroprotection" is meant the relieving, ameliorating, reducing or otherwise decreasing neuroinflammation and neuroinflammatory-promoting conditions. By "non-hormonal" is meant that the molecules do not exhibit hormonal properties. The neuroactive steroids contemplated herein for use in inducing neuroprotection are encompassed by compounds of Formula I which include compounds of Formula II, as herein defined. These compounds include pregnanediones and pregnanediols and enantiomers of progesterone and allopregnanolone which do not bind GABA receptors. Examples include alphaxalone, alphadolone, acebrochol, pregnanolone (eltanolone), ganaxolone, hydroxydione, minaxolone, Org20599, Org21465, as well as synthetic derivatives of allopregnanolone and pharmacologically and pharmaceutically acceptable derivatives, salts and pro-drug forms thereof. The compounds of choice in accordance with the subject method are substantially devoid of hormonal endocrine activity and interact with and activate pregnane X receptor (PXR). PXR is also known as steroid and xenobiotic sensing nuclear receptor (SCR) and as nuclear receptor subfamily 1, group I, member 2 (NR1I2) and is encoded by the NR1I2 gene.

Without limiting the subject disclosure to any particular theory or mode of action, it is proposed herein that the neuroactive steroid activates PXR leading to glycoprotein P receptor activation and elevated levels of $CD^{55}$ which ultimately result in an increase in the rate of clearance of toxins and an inhibition of glial and astrocyte-mediated inflammation.

Hence, the present specification enables a method of inducing neuroprotection in the central nervous system (CNS) in a subject, the method comprising administering to the subject an effective amount of a neuroactive steroid which is substantially devoid of hormonal endocrine activity and which activates a PXR. In an embodiment, the neuroactive steroid is a compound of Formula I. In an embodiment, the neuroactive steroid is a compound of Formula II.

Enabled herein is a method of ameliorating inflammation in the central nervous system (CNS) in a subject, the method comprising administering to the subject an effective amount of a neuroactive steroid which is: (i) devoid of hormonal endocrine activity; and (ii) which activates a pregnane X receptor (PXR).

The neuroactive steroid may be in the form of an anesthetic or sedating composition or as a non-sedating analgesic or neuroprotectant composition. In an embodiment, the subject is a human in need of anesthesia or sedation or exhibiting an adverse neurological condition such as following neurological assault including an infection; hypoxia; asphyxia; chronic pain; chronic opioid therapy; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin.

In an embodiment, the subject being treated has, or is at risk of, developing pain, opioid dependence, opioid tolerance, neruotrauma/surgery, stroke, neurodegenerative disease including Alzheimer's disease and Parkinson's disease or infection (e.g. meningitis).

The present specification is instructional on preventing or ameliorating neuroinflammation leading to neuronal cell death, edema, ischemia and cognitive impairment during anesthesia or sedation or following neurological assault such as outlined above.

In an embodiment, the neuroactive steroid is formulated in a cyclodextrin and is provided in an amount of from about 0.01 mg/kg to about 20 mg/kg/body weight per hour.

The neuroactive steroid may also be administered with an opioid in order to facilitate analgesia without adverse neurological symptoms developing. Alternatively, the neuroactive steroid is coformulated or otherwise administered sequentially or simultaneously with a status such as but not limited to atrovastatin.

The neuroactive steroid may be administered with another drug such as a cholesterol lowering drug including a statin (e.g. atorvastatin) to avoid neuronal dysfunction (e.g. cognitive decline).

Therapeutic kits comprising the neuroactive steroid, packaged for sale or use by a clinician are also taught herein. The kit may further contain an analgesic, a statin or a neurological drug.

In an embodiment, the neuroactive steroid is alphaxalone given as a sedative or anesthetic formulation in a sulfobutyl ether beta-cyclodextrin in a molar ratio of alphaxalone to cyclodextrin of from 1:1.6 to 1:6.

In an embodiment, the neuroactive steroid is alphadolone given in a non-sedating, oral formulation in a sulfobutyl ether beta-cyclodextrin in a molar ratio of alphadolone to cyclodextrin of from 1:2 to 1:6.

Neither alphaxalone or alphadolone exhibits hormonal properties and both activate PXR. Reference to "alphaxalone" and "alphadolone" include derivatives thereof which do not exhibit hormonal properties and which activate PXR receptors.

In an embodiment, the sulfobutyl ether beta-cyclodextrin is (7) sulfobutyl ether beta-cyclodextrin.

BRIEF DESCRIPTION OF THE FIGURES

Some figures contain color representations or entities. Color photographs are available from the Patentee upon request or from an appropriate Patent Office. A fee may be imposed if obtained from a Patent Office.

A1 cremophor/saline vehicle controls (N=15);
B alphadolone (250 mg/kg/day; N=13);
histograms show means and bars±SEM of the TFL expressed as % MPE. Significant tolerance occurred in the vehicle- treated group (*P<0.001) whereas no significant tolerance occurred in the alphadolone-treated rats (P>0.05 one-way ANOVA, Bonferroni post hoc test). ip=intraperitoneal; % MPE=percentage of maximum possible effect.

DETAILED DESCRIPTION

Throughout this specification, unless the context requires otherwise, the word "comprise" or variations such as "comprises" or "comprising", will be understood to imply, the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a neuroactive steroid" includes a single neuroactive steroid, as well as two or more neuroactive steroids; reference to "an anesthetic" includes a single anesthetic, as well as two or more anesthetics; reference to "the disclosure" includes a single and multiple aspects taught by the disclosure; and so forth. Aspects taught and enabled herein are encompassed by the term "invention". All such aspects are enabled within the width of the present invention.

The present disclosure teaches the use of neuroactive steroids, which are: (i) devoid of endocrine hormonal activity; and (ii) which activate human pregnane X receptor (PXR), as neuroprotectants. The neuroactive steroids are proposed to relieve, ameliorate, reduce or otherwise decrease inflammation of the CNS. These neuroactive steroids are useful in anesthetic and sedation formulations such as to induce anesthesia or in non-sedating, analgesic or neuroprotectant formulations. Regardless of the intended use of the neuroactive steroid, the formulations function as neuroprotectants to ameliorate the effects of neuroinflammation otherwise induced by conventional anesthetic or sedating agents or resulting from infection (e.g. meningitis), acute illness, pain, a neurodegenerative condition, hypoxia, asphyxia, or the use of a treatment that alters cholesterol levels and so alters or decreases levels of allopregnanelone within the nervous system, e.g. treatment with atorvastatin and the like. The neuroprotectant formulations are useful for inducing anesthesia or sedation in neonatal, prenatal, postnatal, juvenile and elderly subjects as well as in teenage to middle age subjects. Generally, the subject is a human.

It is proposed to use anesthetic/sedating formulations to induce anesthesia or sedation with minimal long term neuronal dysfunction or disturbance of neurocognitive function and which minimizes induction of neuroinflammation. Non-sedating formulations are also proposed for use as neuroprotecting formulations to reduce neuroinflammation and to increase transport of neurotoxins out of the CNS. Such neuroprotecting formulations are proposed herein to be useful in the treatment or prophylaxis of infection; hypoxia; asphyxia; chronic pain; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin. In an example, the neuroactive steroid is coformulated with or otherwise simultaneously or sequentially with a statin, such as but not limited to atorvastatin.

In an embodiment, the subject being treated has, or is at risk of, developing pain, opioid dependence, opioid tolerance, neruotrauma/surgery, stroke, neurodegenerative disease including Alzheimer's disease and Parkinson's disease or infection.

The compounds of choice in accordance with the subject method are substantially devoid of hormonal endocrine activity and interact with and activate pregnane X receptor (PXR). PXR is also known as steroid and xenobiotic sensing nuclear receptor (SCR) and as nuclear receptor subfamily 1, group I, member 2 (NR1I2) and is encoded by the NR1I2 gene.

Accordingly, enabled herein is a method for inducing neuroprotection in the central nervous system (CNS) in a subject, the method comprising administering to the subject an effective amount of a neuroactive steroid which is devoid of endocrine hormonal activity and which activates a pregnane X receptor (PXR) in the CNS.

Taught herein is a method for inducing anesthesia or sedation in a subject with minimal neuroinflammation which would otherwise lead to long term neuronal dysfunction, the method comprising administering to the subject an effective amount of a neuroactive steroid which is devoid of endocrine hormonal activity and which activates a PXR in the CNS.

The present disclosure is instructional for a method of inducing analgesia in a subject, the method comprising administering to the subject an effective amount of a neuroactive steroid which is devoid of endocrine hormonal activity and which activates a PXR in the CNS, alone or in combination with an opioid.

Further taught herein is a method for treating a subject who has or is suspected of having had an assault of the neurological system, the method comprising administering to the subject an effective amount of a neuroactive steroid which is devoid of endocrine hormonal activity and which activates a pregnane X receptor (PXR) in the CNS.

Further taught herein is a method for treating a subject with a neurodegenerative disease, the method comprising to the subject an effective amount of neuroactive steroid which is devoid of endocrine hormonal activity and which activates a pregnane X receptor (PXR) in the CNS.

Taught herein is a method for administering a statin to a subject with a reduced risk of neuronal dysfunction such as cognitive dysfunction, the method comprising administering to the subject an effective amount of neuroactive steroid which is devoid of endocrine hormonal activity and which activates a pregnane X receptor (PXR) in the CNS, simultaneously or sequentially with the statin. In an example, the statin is atorvastatin.

The above aspects include neuroinflammatory-promoting conditions.

The present specification is instruction for a method of ameliorating inflammation in the central nervous system (CNS) in a subject, the method comprising administering to the subject an effective amount of a neuroactive steroid which is: (i) devoid of hormonal endocrine activity; and (ii) which activates a pregnane X receptor (PXR). In an embodiment, the neuroactive steroid is formulated in a sulfobutyl ether beta-cyclodextrin, such as (7) sulfobutyl ether beta-cyclodextrin or an alkylated derivative thereof.

Examples of neurological assaults include Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, meningitis, herpes or AIDS, or any condition or treatment that disturbs cholesterol metabolism such that production and levels of allopregnanelone are decreased or deficient within the nervous system, e.g. treatment of a subject with atorvastatin. In addition, the neuroactive steroids can be used as anesthetics or sedatives or analgesics without long term neuronal dysfunction. Generally, the subject is a human although the subject method applies to non-human subjects such as for use in clinical trials.

The neuroactive steroid is a compound generally represented by a compound of Formula I:

(I)

wherein:

$R_1$ is hydrogen, amino, thio, sulfinyl, sulfonyl, sulfonamido, halogen, hydroxyl optionally substituted alkoxy, optionally substituted alkyl, optionally substituted alkenyl, optionally substituted alkynyl optionally substituted $C_2$-$C_4$ alkenyl or optionally substituted morpholinyl;

$R_2$ is hydrogen, oxygen (keto), alkyl, hydroxy, alkoxy, alkanoyloxy, aminocarbonyloxy, alkoxycarbonyloxy, morpholinyl, halogen, SCN, $OCOCH_3$, $OCOCH_3$, $OCOCH_2CH_3$, $OCH_3$, $OCH_2CH_3$, $OCH(CH_3)_2$, $OCH_2CH_2CH_2CH_3$, $OC(CH_3)_3$, $CH_2CH_2CH_2CH_3$;

$R_3$ is hydrogen, hydroxy, piperidino, morpholinyl optionally substituted alkyl, optionally substituted alkenyl, optionally substituted alkoxyalkyl, optionally substituted aminoalkyl, cyano, optionally substituted cyanoalkyl, optionally substituted thiocyanoalkyl, isothiocyano, optionally substituted azidoalkyl, optionally substituted alkanoyloxyalkyl, optionally substituted arylalkyl, optionally substituted heteroarylalkyl, optionally substituted arylalkenyl, optionally substituted heteroarylalkenyl, optionally substituted aryl, optionally substituted arylkynyl, optionally substituted arylkylalkynyl, optionally substituted alkanoyloxyalkynyl, optionally substituted heteroaryloxyalkynyl, optionally substituted oxoalkynyl or a ketal thereof, optionally substituted cyanoalkynyl, optionally substituted heteroarylalkynyl, optionally substituted hydroxyalkynyl, optionally substituted alkoxyalkynyl, optionally substituted aminoalkynyl, optionally substituted acylaminoalkynyl, optionally substituted mercaptoalkynyl, optionally substituted hydroxyalkynyl dioic acid hemi-ester or a salt thereof, or optionally substituted alkynyloxyalkynyl including $OCOCH_3$, $SCOCH_3$, $OCH_3$, —$CH_2CH_3$, halogen, $N_3$, sodium salt, piperidino, $OCH_2CH_2$-morpholinyl, $OCOCH_2N(CH_2CH_3)_2$, $SCSOCH_2CH_2$-morpholinyl, citrate; or $R_2$ is oxygen and $R_3$ is alkyl or alkenyl or alkynyl group bonded to $R_2$ to form an oxygenated ring which can be optionally substituted;

$R_4$ is hydrogen, hydroxy or alkyl;

$R_5$ is hydrogen, halogen or hydroxy;

$R_6$ is hydrogen, hydroxy, —$(CH_2)y$-, a $C_{2-5}$ alkenylene group, or a $C_{2-5}$ alkynylene group, wherein y is an integer and can take the value of 1 or 2 or 3 or 4 or 5 and R is $C_1$-$C_6$ alkyl, $C_2$-$C_6$ alkenyl or $C_2$-$C_6$ alkanoyl; and $R_7$ is methyl, hydrogen, hydroxy, halogen, SH, SR, —OR, is —$(CH_2)_n$—, a $C_{2-5}$ alkenylene group, or a $C_{2-5}$ alkynylene group, $C_2$-$C_4$ alkanoyl, wherein n is an integer and can take the value of 0 or 1 or 2 or 3 or 4 or 5 and R is $C_1$-$C_4$ alkyl, $C_2$-$C_4$ alkenyl, $C_2$-$C_4$ alkanoyl, $C_2$-$C_5$ alkenylene, —OR or morpholinyl;

$R_8$ is hydrogen, hydroxy, piperidino, morpholinyl optionally substituted alkyl, optionally substituted alkenyl, optionally substituted alkoxyalkyl, optionally substituted aminoalkyl, cyano, optionally substituted cyanoalkyl, optionally substituted thiocyanoalkyl, isothiocyano, optionally substituted azidoalkyl, optionally substituted alkanoyloxyalkyl, optionally substituted arylalkyl, optionally substituted heteroarylalkyl, optionally substituted arylalkenyl, optionally substituted heteroarylalkenyl, optionally substituted aryl, optionally substituted arylkynyl, optionally substituted arylkylalkynyl, optionally substituted alkanoyloxyalkynyl, optionally substituted heteroaryloxyalkynyl, optionally substituted oxoalkynyl or a ketal thereof, optionally substituted cyanoalkynyl, optionally substituted heteroarylalkynyl, optionally substituted hydroxyalkynyl, optionally substituted alkoxyalkynyl, optionally substituted aminoalkynyl, optionally substituted acylaminoalkynyl, optionally substituted mercaptoalkynyl, optionally substituted hydroxyalkynyl dioic acid hemi-ester or a salt thereof, or optionally substituted alkynyloxyalkynyl including $OCOCH_3$, $SCOCH_3$, $OCH_3$, —$CH_2CH_3$, halogen, $N_3$, sodium salt, piperidino, $OCH_2CH_2$-morpholinyl, $OCOCH_2N(CH_2CH_3)_2$, $SCSOCH_2CH_2$— morpholinyl, citrate; or $R_2$ is oxygen and $R_3$ is alkyl or alkenyl or alkynyl group bonded to $R_2$ to form an oxygenated ring which can be optionally substituted;

$R_9$ is =O (keto or oxygen) or a group which blocks endocrine hormonal activity; and $R_{10}$ is methyl, hydrogen, hydroxy, halogen, SH, SR, —OR, is —$(CH_2)_n$—, a $C_{2-5}$ alkenylene group, or a $C_{2-5}$ alkynylene group, $C_2$-$C_4$ alkanoyl, wherein n is an integer and can take the value of 0 or 1 or 2 or 3 or 4 or 5 and R is $C_1$-$C_4$ alkyl, $C_2$-$C_4$ alkenyl, $C_2$-$C_4$ alkanoyl, $C_2$-$C_5$ alkenylene, —OR or morpholinyl;

or a pharmacologically acceptable derivative, salt or prodrug form thereof.

The term "derivative" includes deuterated and tritiated derivatives of the neuroactive steroid where one or more hydrogen atoms may be replaced by deuterium or tritium. The term derivative includes enantiomers of progesterone which do not bind GABA receptors.

The term "alkyl" denotes straight chain, branched or monocyclic alkyl, generally including from 1 to 6 carbon atoms. Examples of straight chain, branched and cyclic alkyls include methyl, ethyl, propyl, isopropyl, butyl, cyclpropyl and cyclobutyl.

The term "alkenyl" used herein denotes groups formed from straight chain, branched or cyclic alkenes, including mono- or poly-unsaturated alkyl or cycloalkyl groups. Specific examples include vinyl, alkyl, 1-methylvinyl, butenyl and isobutenyl.

The term "alkanoyl" denotes straight or branched chain alkanoyl (COalkyl) groups such as acetyl ($COCH_3$), propionyl ($COCH_2CH_3$), butyryl ($COCH_2CH_2CH_3$) and isobutyryl ($COCH(CH_3)_2$).

The term "alkynyl" denotes a straight chain or branched or cyclic unsaturated group which contains at least one carbon-carbon triple bond. The alkynyl group may be singly or multiply substituted. Generally, an alkynyl group is $C_2$-$C_{16}$ alkynyl group.

The term "heterocycloalkyl" herein denotes a cyclic hydrocarbon group containing one, two, three or four O, N or S atoms or combinations of O, N, S atoms, e.g. oxiranyl, oxetanyl, tetrahydrofuranyl, tetrahydro-2/i-pyranyl, morpholinyl, aziridinyl, azetidinyl, pyrrolidinyl, piperidinyl, tetrahydrothiophenyl, tetrahydro-2H-thiopyranyl. Unless otherwise specifically limited, a heterocycloalkyl group may be unsubstituted, singly substituted or, if possible, multiply substituted, with substituent groups in any possible position.

The term "halo" means halogen such as bromine, fluorine, chlorine, iodine and astatine.

The term "haloalkyl" herein denotes an alkyl group substituted with one or more halogens.

The term "heterocycloalkenyl" herein denotes a cyclic unsaturated hydrocarbon group containing at least one carbon-carbon double bond containing one, two, three or four O, N or S atoms or combinations of O, N, S atoms. Unless otherwise specifically limited, a heterocycloalkenyl group may be unsubstituted, singly substituted or, if possible, multiply substituted, with substituent groups in any possible position.

The term "aryl", alone or in combination, herein denotes an aromatic group which contains at least one ring with conjugated x electrons, carbocyclic aryl groups, and biaryl groups which may be unsubstituted, singly substituted or, if possible, multiply substituted, with substituent groups in any possible position. Examples include $C_2$-$C_{10}$ aryl groups. Typical aryl groups include phenyl, naphthyl, phenanthryl, anthracyl, indenyl, azulenyl, biphenyl, biphenylenyl and fluorenyl groups.

The term "biaryl" represents aryl groups substituted by other aryl groups.

The term "carbocyclic aryl" refers to groups wherein the ring atoms on the aromatic ring are carbon atoms.

The term "thio" herein denotes —$SR_{11}$, where $R_{11}$ is hydrogen, alkyl, alkenyl, alkynyl, aryl, arylalkyl or heteroaryl, all of which may be optionally substituted.

The term "sulfinyl" herein denotes —$SOR_{11}$, where $R_{11}$ is hydrogen, alkyl, alkenyl, alkynyl, aryl, arylalkyl or heteroaryl, all of which may be optionally substituted.

The term "sulfonyl" herein denotes —$SO_2R_{11}$, where $R_{11}$ is hydrogen, alkyl, alkenyl, alkynyl, aryl, arylalkyl or heteroaryl, all of which may be optionally substituted.

The term "sulfonamido" herein denotes —$SO_2NR_{11}R_{12}$ wherein $R_{11}$ and $R_{12}$ are independently hydrogen, alkyl, alkenyl, alkynyl, aryl, arylalkyl or heteroaryl, all of which may be optionally substituted.

The term "heteroaryl" refers to carbon containing 5-14 membered cyclic unsaturated radicals containing one, two, three or four O, N or S atoms and having 6, 10 or 14 π electrons delocalized in one or more rings, e.g., thienyl, benzo[b]thienyl, naphtha[2,3-b]thienyl, thianthrenyl, furyl, pyranyl, isobenzofuranyl, chromenyl, xanthenyl, phenoxanthinyl, 2H-pyrrolyl, imidazolyl, pyrazolyl, pyridyl, pyrimidinyl, pyridazinyl, indolizinyl, isoindolyl, 3H-indolyl, indoyl, indazolyl, purinyl, 4H-quinolizinyl, isoquinolyl, quinolyl, phthazinyl, napthyridinyl, quinazolinyl, cinnolinyl, pterdinyl, 5aH-carbazoyl, carbozoyl, beta-carbolinyl, phenanthridinyl, acrindinyl, oxazolyl, pyrimidinyl, benzimidazolyl, triazolyl, each of which may be optionally substituted as discussed above.

The term "optionally substituted" or "substituted" refers to groups substituted by a below described substituent group in any possible position. Substituent groups for the above moieties useful in the practice of the subject method are those groups that do not significantly diminish the desired biological activity (e.g. interacting with PXR and inducing anesthesia or sedation or potentiating analgesia alone or in combination with an opioid) while removing hormonal endocrine activity. Substituent groups include, for example, lower alkyl (acyclic and cyclic), aryl (carbocyclic aryl and heteroaryl), alkenyl, alkynyl, alkoxy, halo, haloalkyl, amino, alkylamino, dialkylamino, mercapto, alkylthio, alkylsulfinyl, alkylsulfonyl, nitro, alkanoyl, alkanoyloxy, alkanoyloxyalkanoyl, alkoxycarboxy, carbalkoxy, carboxamido, formyl, carboxy, hydroxy, cyano, azido, isocyano, isothiocyano, oxime, keto and cyclic ketals thereof, alkanoylamido, heteroaryloxy, O-aroyl, O-alkylOH, O-alkenylOH, O-alkynylOH, O-alkylNXiX$_2$, O-alkenylNX$_1$X$_2$, O-alkynylNX$_1$X$_2$, NH-acyl, NH-aroyl, $CF_3$, $COOX_3$, $SO_3H$, $PO_3X_1X_2$, $OPO_3X_1X_2$, $SO_2NX_1X_2$, $CONX_1X_2$, wherein $X_1$ and $X_2$ each independently denotes H or alkyl or alkenyl or alkynyl, or $X_1$ and $X_2$ together comprise part of a heterocyclic ring having about 4 to about 7 ring atoms and optionally one additional heteroatom selected from O, N or S, or $X_1$ and $X_2$ together comprise part of an imide ring having about 5 to 6 ring atoms and $X_3$ denotes H, alkyl, alkenyl, alkynyl, hydroxy-lower alkyl or alkyl-$NX_1X_2$.

The term "lower" is referred to herein in connection with organic radicals or compounds containing one up to and including six carbon atoms. Such groups may be straight chain, branched chain, or cyclic.

Examples of a compound of Formula I include pregnanediones and pregnanediols and enantiomers of progesterone and allopregnanolone which do not bind GABA receptors. Particular examples include alphaxalone, alphadolone, acebrochol, pregnanolone (eltanolone), ganaxolone, hydroxydione, minaxolone, Org20599, Org21465, as well as synthetic derivatives of allopregnanolone and pharmacologically and pharmaceutically acceptable derivatives, salts and pro-drug forms thereof.

The compounds contemplated herein are devoid of or substantially devoid of hormonal endocrine activity and interact with and activate PXR.

Contemplated here in is a compound of Formula II:

wherein:

$R_{12}$ is halogen, —$CH_3$, morpholinyl, SCN, hydroxy, $OCOCH_3$, $OCOCH_2CH_3$, $OCH_3$, $OCH_2CH_3$, $OCH(CH_3)_2$, $OCH_2CH_2CH_2CH_3$, $OC(CH_3)_3$, $CH_2CH_2CH_2CH_3$;

$R_{13}$ is $CH_3$, hydroxy, oxygen, —$CH_2CH_3$;

$R_{14}$ is $CH_3$, hydroxy, morpholinyl; and $R_{15}$ is hydrogen, hydroxy, —$CH_3$, $OCOCH_3$, $SCOCH_3$, $OCH_3$, —$CH_2CH_3$, halogen, $N_3$, sodium salt, piperidino, $OCH_2CH_2$-morpholinyl, $OCOCH_2N(CH_2CH_3)_2$, $SCSOCH_2CH_2$-morpholinyl, citrate.

In relation to compounds of Formula II where $R_{12}$ is H; $R_{13}$ is hydroxy; $R_{14}$ is $CH_3$; and $R_{15}$ is H then the compound is alphaxalone and where $R_{12}$ is H; $R_{13}$ is hydroxy; $R_{14}$ is $CH_3$; and $R_{15}$ is —$CH_2OH$ then the compound is alphadolone.

Compounds encompassed by Formulae I and II and related compounds are described in, for example, The Merck Index, Australian Patent No. 698746; U.S. Pat. No. 3,558,608; and GB Patent No. 1,317,184 and 1,317,185. Reference can also be made to Philipps (1975) *J Steroid Biochem* 6:607-613.

The present disclosure enables neuroactive steroid compounds of Formulae I and II which are substantially devoid of endocrine hormonal activity and which activate a PXR receptor and which, depending on the compound and the formulation, induce anesthesia or sedation or are non-sedating compounds for use as analgesic adjuncts and potentiators given alone in neuroprotection compositions. Regardless, the neuroactive steroid component is a neuroprotectant, ameliorating symptoms of neuroinflammation and preventing long term neuronal dysfunction.

The present disclosure further teaches a drug delivery system for a neuroactive steroid neuroprotectant. In an embodiment, the drug delivery system comprises a host carrier in the form of a cyclodextrin or modified form thereof. Reference to "cyclodextrin" includes in one embodiment an α-, β- or γ-cyclodextrin or a modified or derivatized form thereof. Reference to "cyclodextrin" in another embodiment includes a sulfoalkyl ether dextrin such as (7) sulfobutyl ether β-cyclodextrin or an alkyl ether derivative thereof such as a sulfobutyl ether-alkyl ether cyclodextrin. Derivatives of cyclodextrins include methylated, hydroxyalkylated, branched, alkylated, acylated and anionic cyclodextrins. By "alkylated" includes an alkyl ether derivative such as an alkyl ether-alkyl ether cyclodextrin. Particular cyclodextrins contemplated herein are shown in Table 1 (Uekama et al. (1998) *Chem. Rev.* 98: 2045-2076) and include β-cyclodextrin sulfobutyl ethers, ethyl ethers, β-cyclodextrin sulfobutyl ethers (flat), γ-cyclodextrin sulfobutyl ethers and α-cyclodextrin sulfobutyl ethers and their salts (e.g. sodium salts).

The drug delivery system described herein enables a neuroactive steroid protectant to be administered to a subject in a sterilized form. Furthermore, the delivery itself is administered with less pain compared to the intravenous administration of propofol. When the formulation is an anesthetic, it has a therapeutic index greater than 5 (meaning that administration of greater than 5 times the anesthetic dose can lead to death in a test animal). By "greater than 5" means a therapeutic index of between 5 and 200 including 10, 20, 30, 40, 50, 60, 70, 80, 90, 100, 110, 120, 130, 140, 150, 160, 170, 180, 190 and 200 as well as integers or fractions in between. The formulation described by the present disclosure is also storable in a plastic container and is compatible for use in plastic delivery apparatus.

Accordingly, an aspect of the present invention provides a neuroprotectant delivery host/guest composition comprising a cyclodextrin host or modified form thereof with a neuroactive steroid drug, which drug does not exhibit hormonal endocrine activity and activates a PXR receptor.

In an embodiment, the neuroactive steroid is alphaxalone given as a sedative or anesthetic formulation in a sulfobutyl ether beta-cyclodextrin in a molar ratio of alphaxalone to cyclodextrin of from 1:1.6 to 1:6.

In an embodiment, the neuroactive steroid is alphadolone given in a non-sedating, oral formulation in a sulfobutyl ether beta-cyclodextrin in a molar ratio of alphadolone to cyclodextrin of from 1:2 to 1:6.

Neither alphaxalone or alphadolone exhibits hormonal properties and both activate PXR. Reference to "alphaxalone" and "alphadolone" include derivatives thereof which do not exhibit hormonal properties and which activate PXR receptors.

In an embodiment, the sulfobutyl ether beta-cyclodextrin is (7) sulfobutyl ether beta-cyclodextrin.

In an embodiment, the formulation is useful for inducing anesthesia or sedation in human subjects without long term neurocognitive impairment or other neural dysfunction. In an embodiment, the composition is a coformulation of the neuroactive steroid and a statin such as atorvastatin.

In an embodiment, the formulation is non-sedating and is useful as a neuroprotectant to treat neuroinflammation such as arising from infection; hypoxia; asphyxia; chronic pain; chronic opioid use; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin, optionally ip combination with an opioid.

An example of a pharmacologically acceptable salt is alphadolone acetate, which is encompassed by the present disclosure. An example of a derivative of a neuroactive steroid anesthetic is a deuterated or tritiated derivative as well as a derivative encompassed by Formula I or Formula II. A "modified" cyclodextrin includes a derivative of a cyclodextrin.

Another aspect enabled herein is directed to a drug delivery host/guest composition comprising a cyclodextrin host or modified form thereof with a neuroactive steroid anesthetic drug guest selected from a pregnanedione, pregnanediol and an enantiomer of progesterone and allopregnanelone which does not bind to GABA receptors. Particular examples include alphaxaloic, alphadolone, acebrochol, pregnanolone (eltanolone), ganaxolone, hydroxydione, minaxotone, Org20599, Org21465, as well as synthetic derivatives of allopregnanolone and pharmacologically and pharmaceutically acceptable derivatives, salts and pro-drug forms thereof.

Taught herein is a method for inducing anesthesia or sedation in a subject with minimal neuroinflammation or long term neuronal dysfunction such as cognitive impairment, the method comprising administering to the subject an effective amount of a neuroactive steroid which is devoid of endocrine hormonal activity and which activates PXR in the CNS formulated in a cyclodextrin host or modified form thereof.

The present disclosure is instructional for a method of inducing analgesia in a subject, the method comprising administering to the subject an effective amount of a neuroactive steroid which is devoid of endocrine hormonal activity and which activates a PXR in the CNS formulated in a cyclodextrin host or a modified form thereof. In an embodiment, this method further comprises the simultaneous or sequential administration of an opioid.

Further taught herein is a method for treating a subject who has or is suspected of having had an assault of the neurological system, the method comprising administering to the subject an effective amount of a neuroactive steroid which is devoid of endocrine hormonal activity and which activates a PXR in the CNS formulated in a cyclodextrin host or a modified form thereof.

Enabled herein is a method for administering a statin to a subject, the method comprising administering to the subject an effective amount of a neuroactive steroid which is devoid of endocrine hormonal activity and which activates a PXR in the CNS formulated in a cyclodextrin host or a modified form thereof together with the statin. In an embodiment, the statin is atorvastatin.

Examples of an assault of the neurological system is infection; hypoxia; asphyxia; chronic pain; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin. In an embodiment, alphadolone and a statin (e.g. atorvastatin) are coformulated together or are co-administered (simultaneously or sequentially).

Enabled herein is a method for treating neuroinflammation or ameliorating the effects of a neuroinflammatory-promoting condition in a subject, the method comprising administering to the subject alphaxalone or a derivative thereof or alphadolone or a derivative thereof wherein the derivative: (i) does not exhibit hormonal properties; and (ii) activates the PXR receptor, the alphaxalone or alphadolone formulated in a sulfobutyl ether beta-cyclodextrin in a molar ratio of from 1:1.6 to 1:6 for alphaxalone and from 1:2 to 1:6 for alphadolone and wherein alphadolone is orally administered.

The formulation can also initiate rapid induction of anesthesia to surgical levels with similar or more rapid wakening time compared to propofol without long term neuronal dysfunction.

The composition enabled by the present disclosure may be referred to as a neuroprotectant, formulation, host/guest composition, drug delivery system, medicament, anesthetic, sedative or analgesic or analgesic potentiator.

The present disclosure further teaches to mixtures of two or more neuroactive steroid drugs such as a composition comprising alphaxalone and alphadolone and/or alphadolone acetate or their pharmacologically or pharmaceutically acceptable derivatives, salts or pro-drug forms, wherein the formulation does not induce adverse neurological side effects.

A "pharmacologically or pharmaceutically acceptable derivative" is a derivative that still induces neuroprotection whilst not increasing adverse side effects. The term "derivative" includes deuterated or tritiated derivatives where one or more hydrogen atoms are replaced with deuterium or tritium as well as enantiomers of progesterone and allopregnanolone which do not react with GABA receptors. This can lead to improved efficacy. Furthermore, the neuroprotectant agents may be subject to alkylation, alkoxylation, acetylation and/or phosphorylation to generate other derivatives. Other types of derivatives include deuterated or tritiated or other labeled forms useful for monitoring and tracking the neuroprotectant in the body. The terms "derivative" and "modified form" are used interchangeably herein. All such derivatives are encompassed by the compounds of Formula I and Formula II. Salts of alphadolone include alphadolone acetate. Reference to pro-drugs include transported pro-drugs.

In an embodiment, the cyclodextrin is a β-cyclodextrin or a modified form thereof such as but not limited to a sulfoalkyl ether dextrin. A useful sulfoalkyl ether dextrin is (7) sulfobutyl ether β-cyclodextrin. Alkyl ether derivatives are also contemplated such as a sulfoalkyl ether-alkyl ether cyclodextrin. An example of an alkyl ether derivative is a sulfobutyl ether-alkyl ether cyclodextrin. Other cyclodextrins contemplated herein are listed in Table 1 and include methylated, hydroxyalkylated, alkylated, branched, acylated and anionic derivatives.

Accordingly, enabled herein is a composition comprising a sulfoalkyl ether dextrin host or modified form thereof with a neuroactive steroid drug guest the neuroactive steroid drug not exhibiting hormonal endocrine activity and which drug activates PXR.

Taught herein is a method for inducing anesthesia or sedation in a subject with minimal neuroinflammation and long term neuronal dysfunction, the method comprising administering to the subject an effective amount of a neuroactive steroid which is devoid of endocrine hormonal activity and which activates a PXR in the CNS formulated in a sulfoalkyl ether dextrin host.

The present disclosure is instructional for a method of inducing analgesia in a subject, the method comprising administering to the subject an effective amount of a neuroactive steroid which is devoid of endocrine hormonal activity and which activates a PXR in the CNS. This method may further comprise the simultaneous or sequential administration of an opioid.

Further taught herein is a method for treating a subject who has or is suspected of having had an assault on the neurological system, the method comprising administering to the subject an effective amount of a neuroactive steroid which is devoid of endocrine hormonal activity and which activates a PXR in the CNS formulated in a sulfoalkyl ether dextrin host.

Enabled herein is a method of administering a statin to a subject, the method comprising administering to the subject an effective amount of a neuroactive steroid which is devoid of endocrine hormonal activity and which activates a PXR in the CNS formulated in a sulfoalkyl ether dextrin host together with the statin (e.g. atorvastatin).

Examples of a neurological assaults include infection; hypoxia; asphyxia; chronic pain; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin.

As indicated above a useful sulfoalkyl ether dextrin is (7) sulfobutyl ether β-cyclodextrin.

The formulation between the neuroactive steroid and cyclodextrin is generally in a molar ratio of from 1:1 to 1:6 (neuroactive steroid:cyclodextrin), including 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, 1:3, 1:3.1, 1:3.2, 1:3.3, 1:3.4, 1:3.5, 1:3.6, 1:3.7, 1:3.8, 1:3.9, 1:4, 1:4.1, 1:4.2, 1:4.3; 1:4.4, 1:4.5, 1:4.6, 1:4.7, 1:4.8, 1:4.9, 1:5, 1:5.1, 1:5.2, 1:5.3, 1:5.4, 1:5.5, 1:5.6, 1:5.7, 1:5.8, 1:5.9 and 1:6. For alphadolone, the molar ratio is from 1:2 to 1:6.

Accordingly, the present disclosure teaches a drug delivery host/guest composition comprising a cyclodextrin host or modified form thereof with a neuroactive steroid drug guest, wherein the molar ratio of neuroactive steroid to cyclodextrin is from about 1:1 to about 1:6 and wherein the neuroactive steroid drug does not exhibit hormonal endocrine activity and which neuroactive steroid activates PXR.

Taught herein is a method for inducing anesthesia or sedation in a subject with minimal neuroinflammation which would otherwise lead to long term neuronal dysfunction, the method comprising administering to the subject an effective amount of a neuroactive steroid which is devoid of endocrine hormonal activity and which activates a PXR in the CNS formulated in a cyclodextrin wherein the molar ratio of neuroactive steroid to cyclodextrin is from about 1:1 to 1:6.

The present disclosure is instructional for a method of inducing analgesia in a subject, the method comprising administering to the subject an effective amount of a neuroactive steroid which is devoid of endocrine hormonal activity and which activates a PXR in the CNS formulated in a cyclodextrin wherein the molar ratio of neuroactive steroid to cyclodextrin is from about 1:1 to 1:6. This aspect may further comprise the simultaneous or sequential administration of an opioid.

Further taught herein is a method for treating a subject who has or is suspected of having had an assault of the neurological system, the method comprising administering to the subject an effective amount of a neuroactive steroid which is devoid of endocrine hormonal activity and which activates a PXR in the CNS formulated in a cyclodextrin wherein the molar ratio of neuroactive steroid to cyclodextrin is from about 1:1 to 1:6.

Taught herein is a method of administering a statin to a subject the method comprising administering to the subject an effective amount of a neuroactive steroid which is devoid of endocrine hormonal activity and which activates a PXR in the CNS formulated in a cyclodextrin wherein the molar ratio of neuroactive steroid to cyclodextrin is from about 1:1 to 1:6 together with the statin (e.g. atorvastatin).

Examples of an assault of the neurological system include infection; hypoxia; asphyxia; chronic pain; a neurodegenerative condition such as Alzheimer's disease, frontotemporal dementia, dementia with Lewy bodies, Parkinson's disease, amyotrophic lateral sclerosis, hereditary spastic paraparesis, Down's syndrome, Niemann Pick disease type C, spinocerebellar atrophy, Friedrich's ataxia, prion disorder, amyloidosis, multiple sclerosis, Charcot Marie tooth, corticobasal degeneration, progressive supranuclear palsy, Huntington's disease, multiple system atrophy; stroke; ischemia; traumatic brain injury; cerebral edema; destruction of vascular integrity; elevated immune or inflammatory response; demyelinization; lipid peroxidation; retinal detachment; and, peripheral neuropathy caused by genetic abnormalities, diabetes, polio, herpes or AIDS, or any condition or treatment that disturbs cholesterol metabolism such that production and levels of allopregnanelone are decreased or deficient within the nervous system, e.g. treatment of a subject with atorvastatin.

In one embodiment, the (7) sulfobutyl ether β-cyclodextrin comprises less than 100 ppm of a phosphate and has an absorption of less than 0.5 AU due to a drug-degrading enzyme, as determined by UV/VIS spectrophotometry at a wave length of 245 nm to 270 nm for an aqueous solution containing 300 mg of the dextrin per ml of solution in a cell having a 1 cm path length. In an embodiment, the formulation may also be storable in a plastic container. In an embodiment, the formulation comprising the (7) sulfobutyl ether β-cyclodextrin, neuroactive steroid and a statin, such as atorvastatin.

Whilst cyclodextrins form a useful carrier in the formulation of the neuroactive steroids, other carriers may also be used such as polyethoxylated castor oil (CremophorEL).

The anesthetic composition aspect of the present disclosure may in an embodiment comprise a buffer such as a phosphate or tris or citrate phosphate buffer to maintain the pH from about 5.5 to about pH8. This includes pH values of 5.5, 6, 6.5, 7, 7.5 and 8. Alternatively, the composition does not comprise a buffer and the pH being from about pH3 to about pH 9.5 such as pH3, 3.5, 4, 4.5, 5, 5.5, 6, 6.5, 7, 7.5, 8, 8.5, 9 or 9.5.

In a further aspect, the formulations of the present disclosure also include one or more agents such as excipients and/or preservatives, microbial retardants. Other agents may also be included to reduce toxicity. Agents include, for example, EDTA, benzyl alcohol, bisulphites, monoglyceryl ester of lauric acid (Monolaurin), capric acid and/or its soluble alkaline salts or its monoglyceryl ester (Monocaprin), edetate, and capric acid and/or its soluble alkaline salts or its monoglyceryl ester (Monocaprin) and edentate. The formulation may also contain one or more co-polymers to assist in solubility or stability of the anesthetic agent. Examples include hydroxy propyl methyl cellulose (HPMC), polyvinyl pyrollidone (PVP) and/or carboxymethyl cellulose (CMC).

Conveniently, the neuroactive steroid anesthetic is provided at a concentration of from about 0.5 to 100 mg/ml in a saline or water suspension comprising the cyclodextrin. Such a concentration includes 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 mg/ml of drug. As indicated above, the composition is generally formulated so that the molar ratio of neuroactive steroid to cyclodextrin is from about 1:1 to about 1:6, including from about 1:1 to 1:4, including from about 1:1 to 1:3 and including about 1:2. For alphadolone, the molar ratio is from 1:2 to 1:6.

Reference to any particular neuroactive steroid or their salts includes a racemic mixture of enantiomers of each neuroprotectant as well as a single enantiomer of the agent.

In an embodiment, the neuroactive steroid is a pregnanedione, pregnanediol or an enantiomer of progesterone or allopregnanolone which does not bind to GABA receptors and wherein the steroid is devoid of hormonal endocrine activity and which steroid activates a PXR in the CNS. In an embodiment, the neuroactive steroid is alphaxalone, alphadolone and/or alphadolone acetate. In one embodiment, alphaxalone is in the formulation at a concentration of from 1 to 100 mg/ml such as 10 mg/ml. In another embodiment, alphadolone or alphadolone acetate is present at 0.5 to 50 mg/ml such as 3 mg/ml.

The instant specification teaches the use of alphaxalone or alphadolone or their derivatives in the manufacture of a medicament to treat neuroinflammation or ameliorate a neuroinflammatory-promoting condition.

The formulations herein are for in vivo delivery meaning that the neuroactive steroid is delivered by intravenous, sub-cutaneous, intraperitoneal, intrathecal, intramuscular, intravitreal, transdermal, suppository (rectal), pessary (vaginal), inhalation, intranasal and the like. Most effectively, the formulation is an intravenous (iv) formulation. Alphadolone given orally is non-sedating and induces analgesia alone or in combination with an opioid.

Taught herein is an injectable formulation of a neuroactive steroid anesthetic selected to be sterilizable, administrable by intravenous injection with minimal pain, exhibiting a therapeutic index of greater than 5 and storable in a plastic container formulated with cyclodextrin, such as (7) sulfobutyl ether β-cyclodextrin or an alkyl ether derivative wherein the neuroactive steroid does not exhibit hormonal endocrine activity and it activates PXR.

The neuroactive steroid may be used alone or in combination with another anesthetic or sedative or other active agent such as an opioid. In an embodiment, alphaxalone is used with alphadolone or its salt, alphadolone acetate. Hence, reference to "alphadolone" includes alphadolone acetate. The composition may comprise, therefore alphaxalone or alphadolone alone or a combination of alphaxalone and alphadolone or any of their derivatives, salts or pro-drug forms.

In another aspect, the present disclosure teaches a method of inducing analgesia in a subject comprising the concurrent (simultaneous) or sequential administration to the subject in need of such treatment of additively, synergistically effective amounts of a compound of Formula I or II, or a pharmaceutically acceptable derivative, salt or pro-drug form thereof, and another analgesic compound such as an opioid. Thus, a synergistically effective amount of a compound of Formula I or II, or pharmaceutically acceptable derivative, salt or pro-drug form thereof, when administered concurrently or sequentially with an opioid restores opioid responsiveness to pain. The compound of Formula I or II, or pharmaceutically acceptable derivative, salt or pro-drug form thereof, and the opioid may be administered either as a combined form, i.e. a single composition containing the active agents, or as discrete dosages. The active agents are temporally administered such that the desired additive or synergistic analgesic effect is achieved.

As used herein, opioid compounds (opioids) include any compound which is a partial or full agonist of an opioid receptor.

Opioid compounds are well known and include naturally occurring compounds derived from opium such as codeine, morphine and papavarine as well as derivatives of such compounds which generally have structural similarity and other compounds which are active as analgesic agents. Specific examples of opioid compounds contemplated by the present disclosure include: morphine, fentanyl, oxycodone, codeine, dihydrocodeine, dihydrocodeinone enol acetate, desomorphine, apomophine, pethidine, methadone, dextropropoxyphene, pentazocine, dextromoramide, oxymorphone, hydromorphone, dihydromorphine, noscapine, papaverine, papaveretum, alfentanil, buprenophine and tramadol and pharmaceutically acceptable derivatives and/or tautomers.

The phrase "pharmacologically or pharmaceutically acceptable derivative" is intended to convey any pharmaceutically acceptable salt, pro-drug, hydrate, solvate, metabolite or any other compound which, upon administration to the subject, is capable of providing (directly or indirectly) the compound concerned or a physiologically (e.g. analgesically) equivalent active compound, or an active metabolite or residue thereof. An example of a suitable derivative is an ester formed from reaction of an OH or SH group with a suitable carboxylic acid, for example $C_1$-alkyl-$CO_2H$, and $HO_2C-(CH)_n-CO_2H$ (where n is 1-10, including 1-4), and $CO_2H-CH_2phenyl$.

The compounds of Formulae I and II may be in crystalline form, either as the free compounds or as solvates (e.g. hydrates). Methods of solvation are generally known within the art.

The salts of the active compounds of the instant disclosure generally pharmacologically or pharmaceutically acceptable, but it will be appreciated that non-pharmacologically or non-pharmaceutically acceptable salts also fall within the scope of the present invention, since these are useful as intermediates in the preparation of pharmacologically or pharmaceutically acceptable salts. Examples of pharmacologically or pharmaceutically acceptable salts include salts of pharmacologically or pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulfphonic, toluenesulphonic, benzenesulphonic, salicyclic, sulphanilic, aspartic; glutamic, edetic, stearic, palmitic, oleic, lauric, pantothenic, tannic, ascorbic and valeric acids.

The term "pro-drug" is used herein in its broadest sense to include those compounds which can be converted in vivo to the compound of interest (eg by enzymatic or hydrolytic cleavage). Examples thereof include esters, such as acetates of hydroxy or thio groups, as well as phosphates and sulphonates. Processes for acylating hydroxy or thio groups are known in the art, e.g. by reacting an alcohol (hydroxy group), or thio group, with a carboxylic acid. Other examples of suitable pro-drugs are described in Bundgaard (1985) *Design of Prodrugs*, Elsevier.

The term "metabolite" includes any compound into which a compound of Formula I or Formula II can be converted in vivo once administered to the subject. Examples of such a metabolite are a glucuronide, a sulphate and hydroxylates.

It will be understood that the compounds as described herein may exist in a tautomeric form to that depicted, i.e. as a tautomer thereof. The term "tautomer" is used herein in its broadest sense to include compounds which are capable of existing in a state of equilibrium between two isomeric forms. Such compounds may differ in the bond connecting two atoms or groups and the position of these atoms or groups in the compound. A specific example is keto-enol tautomerism.

The compounds of the instant disclosure may be electrically neutral or be polycations with associated anions for electrical neutrality. Suitable associated anions include sulfate, tartrate, citrate, chloride, nitrate, nitrite, phosphate, perchlorate, halosulfonate or trihalomethylsulfonate.

As used herein, an "effective amount" refers to an amount of active compound which provides the desired analgesic activity when administered according to a suitable dosing regime. The amount of a compound of Formula I or Formula II, or pharmacologically or pharmaceutically acceptable derivative thereof is an amount which provides the desired analgesic, anesthetic or sedation activity without causing overt sedation. Dosing may occur at intervals of minutes, hours, days, weeks or months. Suitable dosage amounts and regimes can be determined by the attending physician or veterinarian. For example, compounds of Formula I or Formula II, or pharmacologically or pharmaceutically acceptable derivatives thereof, may be administered to a subject at a rate of 50 to 2000 mg every six hours, such as 50-500 mg. Dosing of the analgesic agent, such as an opioid, can be determined by the attending physician in accordance with dosing rates in practice. For example, fentanyl can be administered in an amount of about 10-100 μg whereas morphine may be administered in an amount of 1-100 milligrams. In an embodiment, the neuroactive steroid is provided in an amount of from about 0.01 mg/kg to about 20 mg/kg/body weight per hour.

The latter includes 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 and 20 mg/kg/body weight per hour.

The compositions enabled herein comprise at least one compound of Formula I or Formula II or a pharmacologically or pharmaceutically acceptable derivative thereof, optionally with an analgesic compound such as an opioid, together with one or more pharmacologically or pharmaceutically acceptable additives such as carriers, diluents adjuvants and/or excipients and optionally other medicaments. These include all conventional solvents, dispersion agents, fillers, solid carriers, coating agents, antifungal or antibacterial agents, dermal penetration agents, surfactants, isotonic and absorption agents and slow or controlled release matrices. Compositions for use in the subject method may also include other supplementary physiologically active agents, e.g. other analgesic agents. The compounds may be presented in the form of a kit of components which is adapted for allowing concurrent or sequential administration of the active components. Each carrier, diluent, adjuvant and/or excipient must be pharmacologically or pharmaceutically "acceptable" in the sense of being compatible with the other ingredients of the composition and not injurious to the subject. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

Compositions enabled herein suitable for oral administration (e.g. alphadolone) may be presented as discrete units such as capsules, sachets or tablets each containing a predetermined amount of the active ingredient; as a powder or granules; as a solution or a suspension in an aqueous phase or non-aqueous liquid; or as an oil-in-water liquid emulsion or a water-in-oil emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent, preservative disintegrant (e.g. sodium starch glycollate, cross-linked povidone, cross-linked sodium carboxymethyl cellulose) surface-active or dispersing agent. Moulded tablets may be made my moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspended agents and thickening agents. The compositions may be presented in a unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compositions suitable for topical administration to the skin, i.e. transdermal administration, may comprise the active compounds dissolved or suspended in any suitable carrier or base and may be in the form of lotions, gels, creams, pastes, ointments and the like. Suitable carriers may include mineral oil, propylene glycol, waxes polyoxyethylene, and long chain alcohols. Transdermal devices, such as patches may also be used and may comprise a microporous membrane made from suitable material such as cellulose nitrate/acetate, propylene and polycarbonates. The patches may also contain suitable skin adhesive and backing materials.

The compounds of Formula I or Formula II may also be presented as implants which may comprise a drug bearing polymeric device wherein the polymer is biocompatible and non-toxic. Suitable polymers may include hydrogels, silicones, polyethylenes and biodegradable polymers.

The compounds for use herein may be administered in a sustained (i.e. controlled) or slow release form or by infusion. A sustained release preparation is one in which the active ingredient is slowly released within the body of the subject once, administered and maintains the desired drug concentration over a minimum period of time. The preparation of sustained release formulations is known to the skilled person. Dosage forms may include oral forms, implants and transdermal forms. For slow release administration, the active ingredients may be suspended as slow release particles or within liposomes, It should be understood that in addition to the ingredients particularly mentioned above, the subject formulation may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Other details of pharmaceutically acceptable carriers, diluents and excipients and methods of preparing pharmaceutical compositions and formulations are provided in Remington's Pharmaceutical Sciences 18 Edition (1990) Mack Publishing Co., Easton, Pa., USA, the disclosure of which is included herein in its entirety by way of reference.

The compounds for use in accordance with the subject method may also be presented for use in veterinary compositions. These may be prepared by any suitable means known in the art. Examples of such compositions include those adapted for:

(a) oral administration, e.g. drenches including aqueous and non-aqueous solutions or suspensions, tablets, boluses, powders, granules, pellets for admixture with feedstuffs, pastes for application to the tongue;

(b) parenteral administration, e.g. subcutaneous, intramuscular or intravenous injection as a sterile solution or suspension;

(c) topical application, e.g. creams, ointments, gels, lotions, etc.

Useful compounds according to Formula I or Formula II include pregnanediones and pregnanediols and enantiomers of progesterone and allopregnanolone which do not bind GABA receptors. Particular examples include alphaxalone, alphadolone, acebrochol, pregnanolone (eltanolone), ganaxolone, hydroxydione, minaxolone, Org20599, Org21465, as well as synthetic derivatives of allopregnanolone and pharmacologically and pharmaceutically acceptable derivatives, salts and pro-drug forms thereof.

In an embodiment the compound according to Formula I or Formula II is administered orally, such as in the form of a tablet, capsule, lozenge or liquid. The administered composition includes a surfactant and/or solubility improver.

The formulation may be packaged for sale with instructions for use. The use includes a patient management protocol comprising administering to the patient an effective amount of neuroactive steroid such as selected from alphaxalone, alphadolone and pharmacologically acceptable derivatives, salts and pro-drug forms thereof formulated with a cyclodextrin such as a sulfoalkyl ether dextrin, for example, (7) sulfobutyl ether β-cyclodextrin, for a time and under conditions sufficient to induce anesthesia. In another embodiment, the formulation or kit comprising active agents comprises a cyclodextrin, a neuroactive steroid and a statin.

In terms of an anesthetic-effective amount, this is generally around 0.25 mg/kg to about 100 mg/kg body weight. A sedative-effective amount is provided in similar or lower amounts and includes from about 0.05 mg/kg to about 10 mg/kg body weight.

The present disclosure further enables a kit. The kit may be in any form including a syringe or modified syringe. A kit may comprise a pregnanedione, pregnandiol or an enantiomer of progesterone or allopregnanolone which do not bind GABA receptors.

Examples include alphaxalone and/or alphadolone or other neuroactive steroid anesthetic or their derivatives, salts or pro-drug forms in one or more compartments and a sulfoalkyl ether dextrin in a further compartment as well as excipients in subsequent compartments. The contents of the compartments may be admixed prior to use. The neuroactive steroid is substantially devoid of hormonal endocrine activity but activate PXR with CNS.

In an embodiment, the present disclosure teaches a formulation comprising alphaxalone and/or alphadolone and/or pharmacologically acceptable derivatives, salts or pro-drug forms thereof complexed with the sulfobutyl ether cyclodextrin, for use in inducing or maintaining by infusion or intermittent bolus administration, anesthesia or sedation in a human subject without long term neuronal dysfunction.

The anesthetic forms may be labeled such as deuterated or tritiated forms or by other labels to facilitate monitoring and tracking of the anesthetics in the body. Kits and apparatus are provided, therefore, to monitor labeled neuroactive steroid anesthetics.

Whilst the present disclosure teaches anesthetic formulations for use in humans, the formulations may also be used in animals such as for clinical trials or veterinary use. Non-human animals contemplated herein include rats, mice, guinea pigs, hamsters, sheep, pigs, dogs, cats, horses, cows, goats, camels and non-human primates.

Hence, the present disclosure enables an anesthetic or sedative or analgesic or neuroprotectant composition comprising a neuroactive steroid which is devoid of hormonal endocrine activity but which activates a PXR in the CNS and a cyclodextrin or modified form thereof wherein the composition has the following properties:

(i) the neuroactive steroid and cyclodextrin are formulated in a molar ratio of from about 1:1 to about 1:6;
(ii) the neuroactive steroid is selected from a compound of Formula I or Formula II including alphaxalone, alphadolone, acebrochol, allopregnanolone, eltanolone (pregnanolone), ganaxolone, hydroxydione, minaxolone, Org20599, Org21465 and a pharmacologically acceptable derivative, salt or pro-drug form thereof formulated;
(iii) the cyclodextrin is selected from an α-, β-, and γ-cyclodextrin or a modified form thereof;
(iv) a buffer is optionally present and when present the pH of the formulation is from about pH5.5 to about pH8.0 and in the absence of buffer, the pH is from about pH3 to about pH9.5;
(v) the formulation is sterilizable;
(vi) intravenous injection of the formulation induces less pain than from a propofol formulation;
(vii) the therapeutic index of an anesthetic formulation which is greater than 5;
(viii) the formulation can be stored in a plastic container; and
(ix) the formulation can initiate rapid induction of anesthesia to surgical levels with similar or more rapid wakening time compared to propofol.

In an embodiment, an anesthetic or sedative or non-sedating analgesic or neuroprotectant formulation is provided comprising a sulfoalkyl ether or sulfoalkyl ether-alkyl ether dextrin, a neuroactive steroid anesthetic such as alphaxalone or alphadolone and one or more co-polymers such as HPMC, PVP and/or CMC wherein the formulation does not cause long term neuronal dysfunction such as cognitive impairment.

In an embodiment, the neuroactive steroid is coformulated with a statin.

In an embodiment, the neuroactive steroid anesthetic is formulated with a sulfoalkyl ether dextrin such as (7) sulfobutyl ether β-cyclodextrin.

The present disclosure teaches a method for formulating a neuroprotectant composition, the method generating a host/guest composition comprising a cyclodextrin and a neuroactive steroid which neuroactive steroid is substantially devoid of hormonal endocrine activity but which activates a PXR in the CNS. In an embodiment, the cyclodextrin is a sulfoalkyl ether or sulfoalkyl ether-alkyl ether dextrin such as (7) sulfobutyl ether β-cyclodextrin or sulfobutyl ether-alkyl ether β-cyclodextrin. Other cyclodextrins include β-cyclodextrin sulfobutyl ether-ethyl ether, β-cyclodextrin sulfobutyl ether (flat), γ-cyclodextrin sulfobutyl ether, α-cyclodextrin sulfobutyl ether and their sodium salts.

Aspects enabled and taught herein are now further described by the following non-limiting Examples.

EXAMPLES

Example 1

Cardiac Arrest Model of CNS Hypoxia

The following data are taken from a paper that was published in Cervantes et al. (1989) *Bol Estud Med Biol* 37:17-27. The effect of Althesin (Registered) on neurological injury following acute cerebral ischemia induced by an 8 minutes cardiorespiratory arrest (CRA) was investigated by analysis of neurological deficit scores and EEG. The main active ingredient of Althesin (Registered) was alphaxalone which was administered at a dosage appropriate for anaesthesia (10 mg/kg). Two groups of cats were studied: (1) untreated, which received saline iv instead of Althesin (Registered), 7-9 min after the end of CRA and successful resuscitation within 4 minutes thereafter; (2) treated, which received Althesin (Registered) iv, 7-9 min after the end of CRA and successful resuscitation within 4 minutes thereafter.

Figure 1:
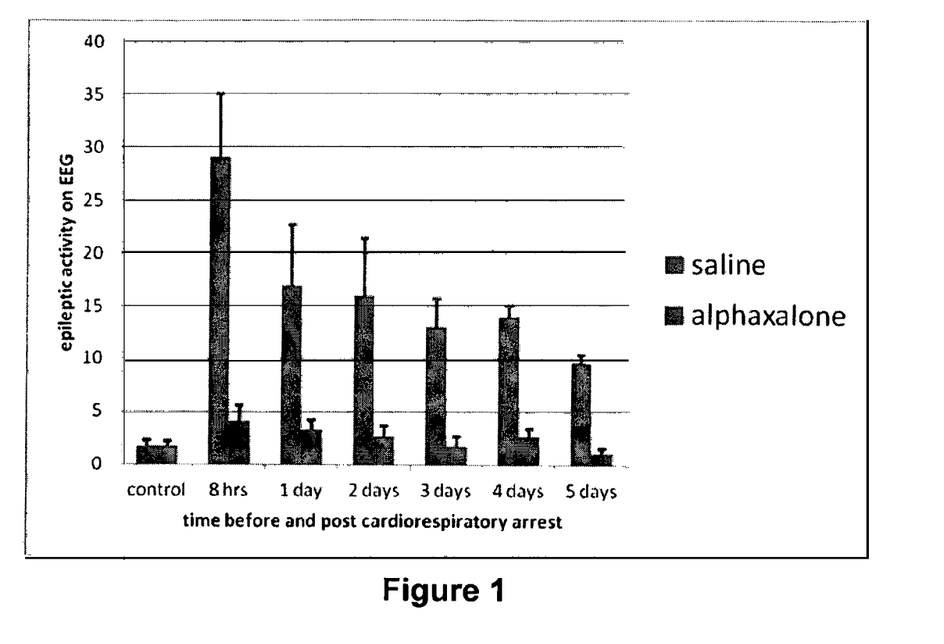
FIG. 1 is a graphical representation showing epileptic activity after cardiac arrest.
Figure 2:
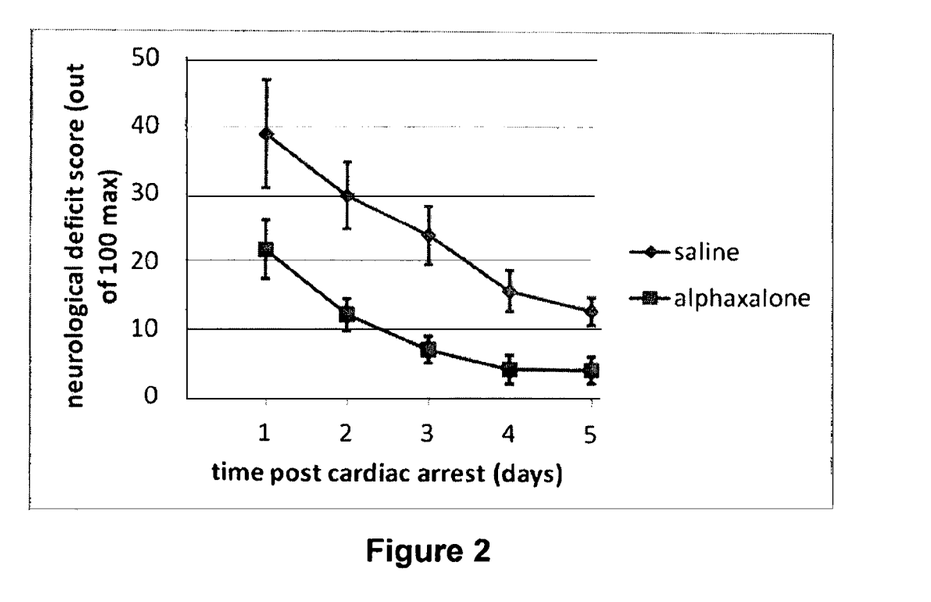
FIG. 2 is a graphical representation showing neurological deficit after cardiac arrest.

Neuromuscular blockade and mechanical ventilation were maintained until 8 h following the CRA. The cats were then allowed to recover spontaneous respiratory activity. The authors performed measurements of EEG activity and neurological function for five days. They found that the recordings of brain electrical activity (EEG) and neurological deficits in untreated and treated cats in the 5 days following CRA were significantly different. In untreated cats, there was high frequency burst-like (epileptic) activity indicative of neurological damage post CRA; see FIG. 1. By contrast, administration of Althesin (Registered) resulted in burst suppression EEG pattern during 1 h after the drug. Progressive recovery of background EEG activity occurred afterwards in this Althesin (Registered) treated group with EEG frequency distributions being the same before and after the CRA; see FIG. 1. Neurological deficit scores were significantly higher in untreated than in treated rats in the five days following the CRA (p<0.01) indicating the persistence of better brain functional conditions after the CRA in cats treated with Althesin (Registered) [alphaxalone] compared with untreated cats; see FIG. 2.

Figure 5:
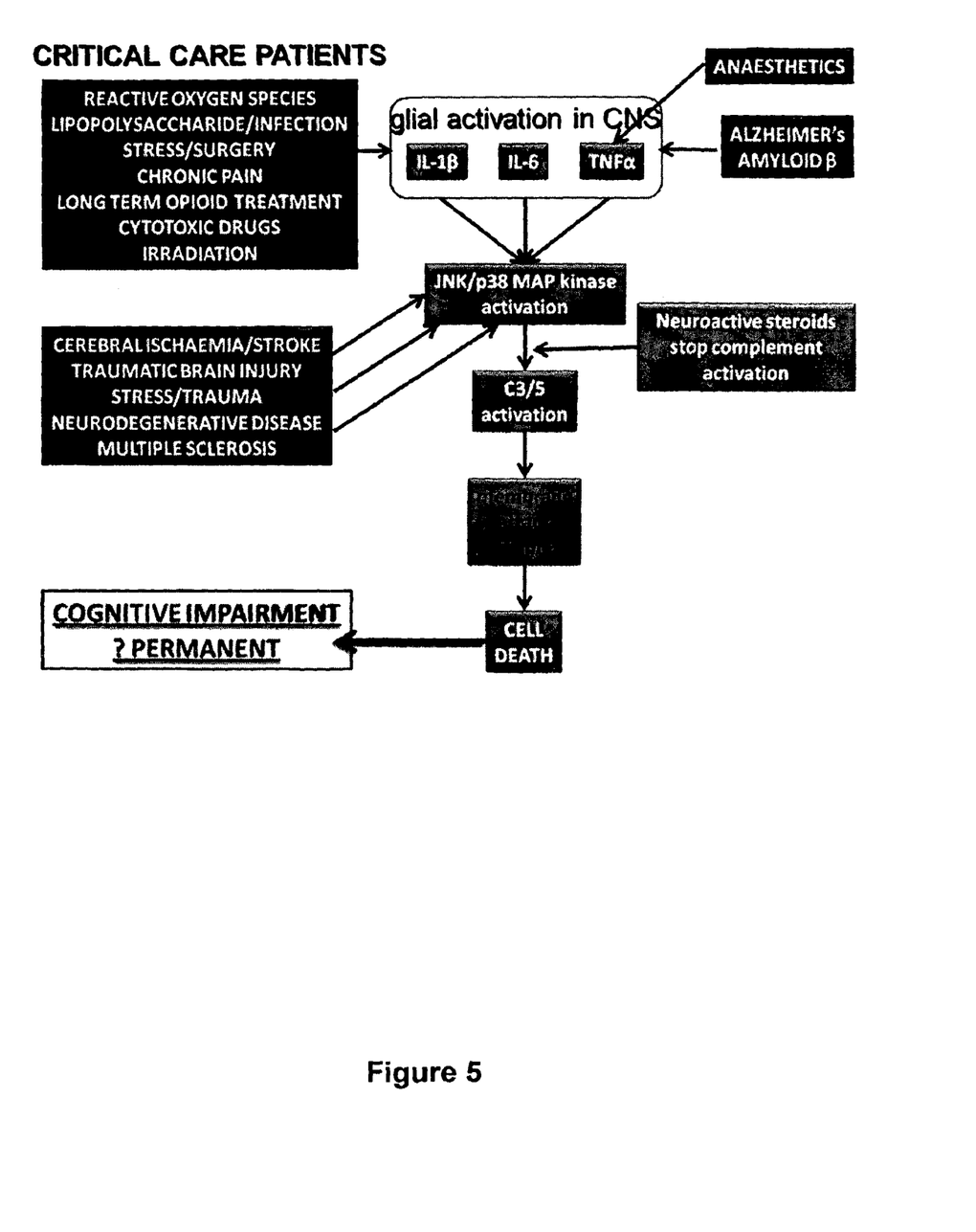
FIG. 5 is a diagrammatical representation showing mechanisms of neuroinflammation.

Normal anaesthesia with alphaxalone (Althesin [Registered]) causes neuroprotection from hypoxia. The mechanism for this effect is shown in FIG. 5.

Example 2

Potassium Cyanide Model of CNS Hypoxia

A general pharmacological screen was performed on the neuroactive steroid alphadolone. Data are presented in Table 2.

TABLE 2

| Test | species | dose | result |
|---|---|---|---|
| depression of behaviour | mouse | 300 mg/kg po | no sedation |
| maximum tolerated dose autonomic signs | mouse | 300 mg/kg po | slight increased sensitivity to touch and exploratory behaviour; slight body temperature elevation |
| hypoxia KCN test | mouse | 100 mg/kg po | result = 50; [≥50% indicates significant cerebral protection] |

Non-sedating doses of the neuroactive steroid alphadolone, given orally, protect the brain from histotoxic hypoxia.

Example 3

Alphaxalone Anesthesia and Fetal Brain

The following has been taken from the following publication Yawno et al. (2009) *Neuroscience* 163:838-847. The aim of this study was to investigate effects on cell death in the brain of late gestation foetal sheep after inhibition of allopregnanolone synthesis using finasteride, a 5α-reductase type 2 (5α-R2) inhibitor. Catheters were implanted in foetal sheep at 125 days of gestation. At 3-4 days post surgery, foetuses received infusions of either finasteride (20 mg/kg/h; n=5), alphaxalone, a neuroactive steroid intravenous anaesthetic which is also an allopregnanolone analogue (5 mg/kg/h which is a normal anaesthetic dose; n=5), or finasteride and alphaxalone together (n=5).

Figure 3:
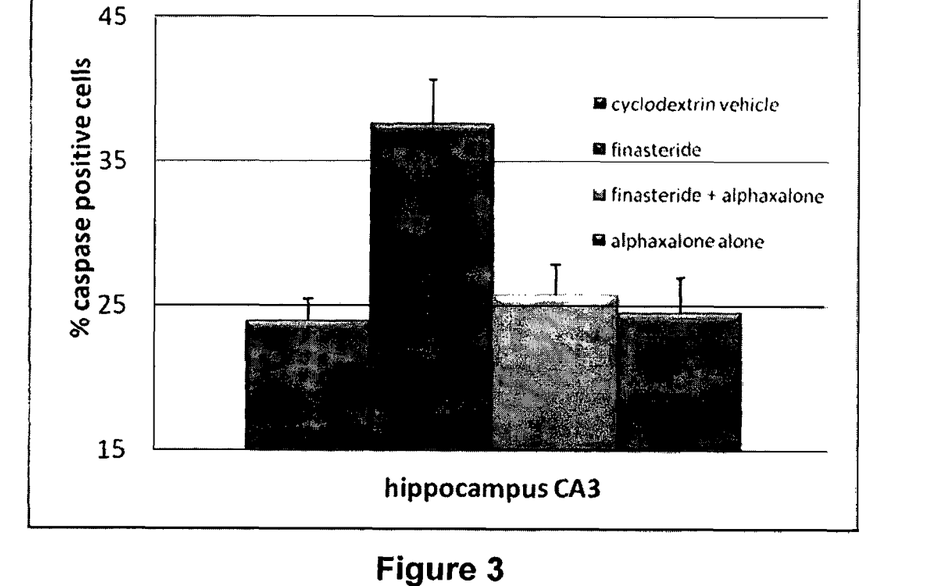
FIG. 3 is a graphical representation showing apoptosis rate in hippocampus.

Brains were obtained at 24 h after infusion to determine cell death (apoptotic or necrotic) in the hippocampus and cerebellum, areas known to be susceptible to excitotoxic damage. Finasteride treatment significantly increased apoptosis (activated caspase-3 expression) in hippocampal CA3 and CA1, and cerebellar molecular and granular layers, an effect abolished by co-infusion of alphaxalone with the finasteride; see FIG. 3. It is also interesting to note that, unlike all other anaesthetic agents in current use, alphaxalone given alone caused no apoptosis; see FIG. 3. Double-label immunohistochemistry showed that both neurones and astrocytes were caspase-3 positive (apoptotic).

Figure 4:
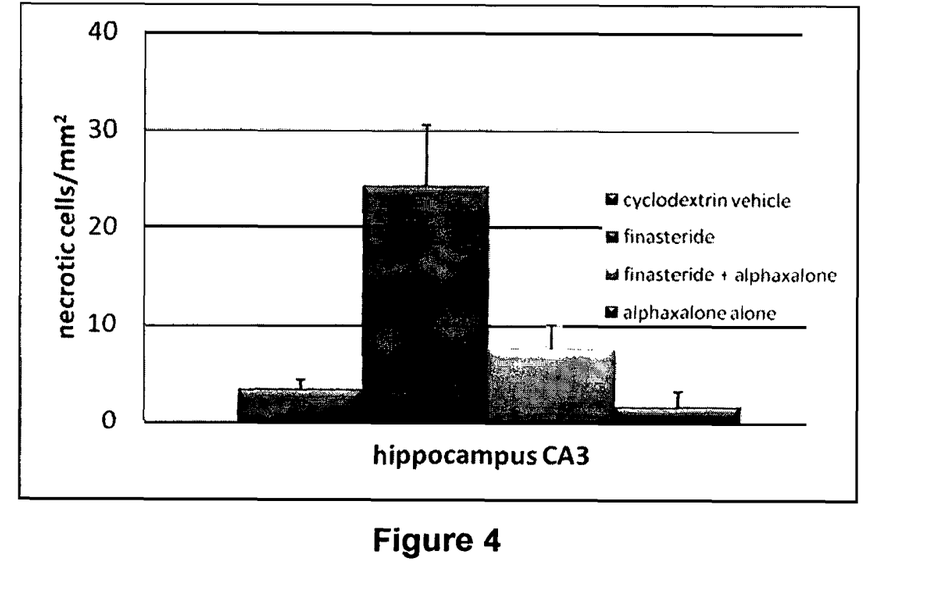
FIG. 4 is a graphical representation showing cell death rate in hippocampus.

Finasteride treatment also increased the number of dead cells in the hippocampus and cerebellum (Purkinje cells), but not when finasteride and alphaxalone were infused together or when alphaxalone was given on its own; see FIG. 4.

Alphaxalone, given at normal anaesthetic doses causes neuroprotection in foetal brain and it can substitute for allopregnanolone in this role. Further, unlike all other anaesthetics in clinical use, alphaxalone does not cause neuronal damage when administered alone at anaesthetic doses.

Example 4

Morphine Tolerance

A simplified scheme of the mechanisms involved with activation of neuroinflammatory processes and subsequent neuronal damage and cognitive deficit are shown in FIG. 5. Central to the activation of complement (C3/5 complex) is activation of the p38 MAPKinase pathway. It can be seen in FIG. 5 that neuroactive steroids interrupt this pathway at the final step (C3 activation) and thus inhibit neuroinflammatory processes and subsequent neuronal damage and cognitive deficit caused by a variety of stimuli, including surgery, pain and chronic opioid use. It is the latter which is the subject of this example.

Opioids are widely used for clinical pain management. However, long-term use of opioids leads to tolerance and limits their use. Patients with morphine tolerance typically require a much higher dose for effective pain control (Duttaroy et al. (1995) *Anesthesiology* 82:1226-36). Microglia have been shown to play the main role of cytokine release upon activation in the central nervous system and there is strong evidence has suggested that non neuronal cells are crucial for morphine tolerance development (Aloisi (2001) *Glia* 36:165-79; Johnston et al. (2004) *J Neurosci* 24:7353-65). Repeated morphine administration leads to release of proinflammatory cytokines TNF-α, IL-1β, and IL-6 from astrocytes and microglia by extracellular signal-regulated kinase (ERK) and p38 (MAPK) [Wang et al. (2009) *Faseb J* 3:2576-86]. Shen et al. (2011) *Anesthesia & Analgesia* February 112(2):454-459 showed that administration of the tumour necrosis factor (TNF)-α antagonist, etanercept to morphine tolerant rats inhibited microglia activation and proinflammatory cytokine production, and reversed the morphine tolerance.

Etanercept Restores the Antinociceptive Effect of Morphine and Suppresses Spinal Neuroinflammation in Morphine-Tolerant Rats.

It can be concluded from this study that the inflammatory process shown in FIG. 5 is also responsible for morphine tolerance. In other words, the same pathways shown in FIG. 5 for the cause of neurodegeneration triggered by the stimuli in the black boxes, are the same as those involved with the cause for morphine tolerance. Thus, if one can demonstrate that a neuroactive steroid devoid of hormonal activity prevents morphine tolerance, this indicates that such a compound will prevent that same mechanism causing neuronal damage when activated by stress, hypoxia, sepsis, surgery, pain, anaesthetic drugs or neurodegenerative disease—FIG. 5. Indeed it has already been shown that neuroactive steroids with endocrine hormonal properties (allopregnanolone, pregnenolone and dehydrepiandrsterone) do prevent morphine tolerance (Reddy and Kulkarni (1997) *Eur J Pharmacol* 337(1):19-25).

Example 5

Morphine Tolerance

This Example shows that alphadolone, a neuroactive steroid with great molecular structural similarity to allopregnanolone, but without any endocrine hormonal properties, prevents morphine tolerance.

The following is taken from Goodchild et al. (2009) *Pain Med* 10: 890-901, morphine tolerance was induced in rats with subcutaneous sustained release morphine emulsion (M-SR; 125 mg/kg/day). Tolerance was assessed by a blinded observer using tail flick latency (TFL) response to intraperitoneal (ip) injection of immediate release morphine (M-IR 6.25 mg/kg). Fifty-five rats given M-SR were divided into three groups: Group A received 1.0 mL subcutaneous emulsion containing vehicle; Groups B had 250 mg/kg alphadolone emulsion injected subcutaneously at the same time as the M-SR. The authors reported that this dose of alphadolone did not cause sedation.

Figure 6:
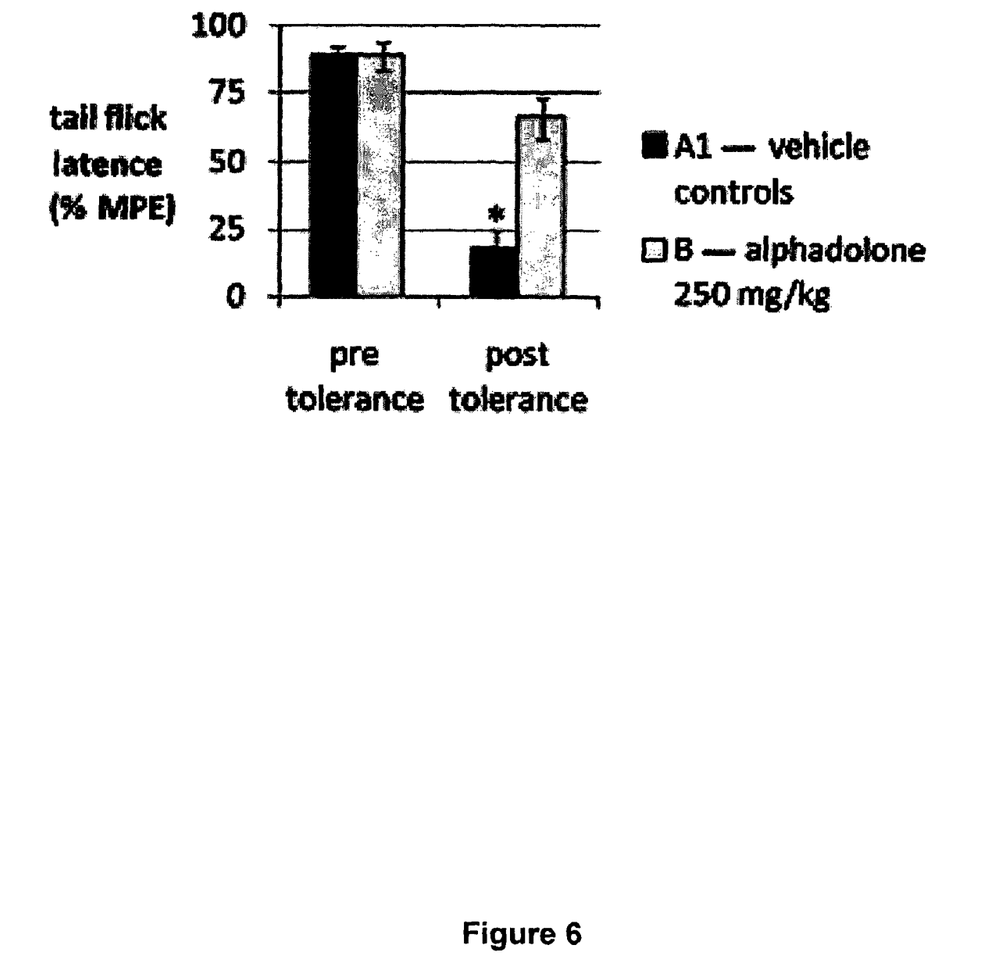
FIG. 6 is a graphical representation of the histograms which show the results of the tail flick latency (TFL) test in response to 6.4 mg/kg ip immediate release morphine in rats on day one (pre-tolerance) before and on day three (post-tolerance) after they had received a two-day treatment with subcutaneous morphine emulsion injections in combination with subcutaneous sustained release emulsions containing.

The results showed that tail flick latency responses (percentage of maximum possible effect [% MPE]) to M-IR were reduced from 89.6±2.5 pre treatment to 20.3±4.8 after M-SR treatment (mean±SEM; P<0.001, one-way ANOVA)-FIG. 6. Co administration of alphadolone emulsion with the M-SR caused no sedation and prevented the occurrence of morphine tolerance, FIG. 6.

Alphadolone can prevent morphine tolerance and since the same mechanisms are involved with neurodegeneration, alphadolone has potential for use as a neuroprotective agent. The lack of sedation suggests clinical utility in human pain states requiring morphine which, when used alone causes morphine tolerance, neuroinflammation and subsequent and neurodegeneration with cognitive decline.

Example 6

Coformulations with Statins

The neuroactive steroid, alphadolone, is coformulated with atorvastatin in (7) sulfobutyl ether β-cyclodextrin and used to reduce cholesterol levels with no long term neuronal dysfunction such as cognitive impairment.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

TABLE 1

Cyclodextrin structures

Primary Hydroxyl Face

Secondary Hydroxyl Face

| compd | $R_1$ | $R_2$ | $R_3$ |
|---|---|---|---|
| Hydrophilic Derivatives | | | |
| methylated cyclodextrins | | | |
| 3-mono-O-methylcyclodextrins | H | $CH_3$ | H |
| 2,6-di-O-methylcyclodextrins | $CH_3$ | H | $CH_3$ |
| 2,3,6-tri-O-methylcyclodextrins | $CH_3$ | $CH_3$ | $CH_3$ |
| randomly methylated cyclodextrins | $R_1, R_2, R_3$ = H or $CH_3$ | | |
| hydroxylalkylated cyclodextrins | | | |
| 2-hydroxyethylcyclodextrins | $R_1, R_2, R_3$ = H or $CH_2CH_2OH$ | | |
| 2-hydroxypropylcyclodextrins | $R_1, R_2, R_3$ = H or $CH_2CH(OH)CH_3$ | | |
| 3-hydroxypropylcyclodextrins | $R_1, R_2, R_3$ = H or $CH_2CH_2CH_2OH$ | | |
| 2,3-dihydroxypropylcyclodextrins | $R_1, R_2, R_3$ = H or $CH_2CH(OH)CH_2OH$ | | |
| branched cyclodextrins | | | |
| 6-O-glucosylcyclodextrins | H | H | H or glucose |
| 6-O-maltosylcyclodextrins | H | H | H or maltose |
| 6-O-dimaltosylcyclodextrins | H | H | H or (maltose)$_2$ |

TABLE 1-continued

Hydrophobic Derivatives alkylated cyclodextrins

| | | | |
|---|---|---|---|
| 2,6-di-O-ethylcyclodextrins | $C_2H_5$ | H | $C_2H_5$ |
| 2,3,6-tri-O-ethylcyclodextrins | $C_2H_5$ | $C_2H_5$ | $C_2H_5$ | acylated cyclodextrins

| | | | |
|---|---|---|---|
| 2,3-di-O-hexanoylcyclodextrins | $COC_5H_{11}$ | $COC_5H_{11}$ | H |
| 2,3,6-tri-O-acetylcyclodextrins | $COCH_3$ | $COCH_3$ | $COCH_3$ |
| 2,3,6-tri-O-propanoylcyclodextrins | $COC_2H_5$ | $COC_2H_5$ | $COC_2H_5$ |
| 2,3,6-tri-O-butanoylcyclodextrins | $COC_3H_7$ | $COC_3H_7$ | $COC_3H_7$ |
| 2,3,6-tri-O-valerylcyclodextrins | $COC_4H_9$ | $COC_4H_9$ | $COC_4H_9$ |
| 2,3,6-tri-O-hexanoylcyclodextrins | $COC_5H_{11}$ | $COC_5H_{11}$ | $COC_5H_{11}$ |
| 2,3,6-tri-O-octanoylcyclodextrins | $COC_7H_{15}$ | $COC_7H_{15}$ | $COC_7H_{15}$ |

Ionizable Derivatives anionic cyclodextrins

| | | | |
|---|---|---|---|
| 6-O-(carboxymethyl)cyclodextrins | H | H | H or $CH_2COONa$ |
| 6-O-(carboxymethyl)-O-ethylcyclodextrins | $C_2H_5$ | $C_2H_5$ | H, $C_2H_5$ or $CH_2COONa$ |
| cyclodextrin sulfates | $R_1, R_2, R_3$ = H or $SO_3Na$ | | |
| sulfobutylcyclodextrins | $R_1, R_2, R_3$ = H or $(CH_2)_4SO_3Na$ | | |

$^a$N = 6, α-CDs; N = 7, β-CDs; N = 8, γ-CDs; N = 9, δ-CDs.

BIBLIOGRAPHY

Aloisi (2001) *Glia* 36:165-79
Briner et al. (2010) *Anesthesiolgy* 112:546-556
Bundgaard (1985) *Design of Prodrugs*, Elsevier
Cervantes et al. (1989) *Bol Estud Med Biol* 37:17-27
Duttaroy et al. (1995) *Anesthesiology* 82:1226-36
Ek et al. (2010) *Toxicol Lett* 197:61-59
Goodchild et al. (2009) *Pain Med* 10: 890-901
Johnston et al. (2004) *J Neurosci* 24:7353-65
Philipps (1975) *J Steroid Biochem* 6:607-613
Reddy and Kulkarni (1997) *Eur J Pharmacol* 337(1):19-25
Remmingtons Pharmaceutical Sciences 18$^{th}$ Edition (1990) Mack Publishing Co., Easton, Pa., USA
Sanders et al. (2009) *Anesthesiology* 110:1077-1085
Selye (1971) *J Pharm Sci* 60:1-28
Shen et al. (2011) *Anesthesia & Analgesia* February 112(2): 454-459
Tan et al. (2009) *Chin. Med J. (Engl)* 122:455-459
Uekama et al. (1998) *Chem. Rev.* 98: 2045-2076
Wang et al. (2009) *Faseb J* 3:2576-86
Yawno et al. (2009) *Neuroscience* 163:838-847
Zhu et al. (2010) *J. Cereb. Blood Flow Metabl* 30:1017-1030

The invention claimed is:

1. A method of treating inflammation or ameliorating a neuroinflammatory-promoting condition in the central nervous system (CNS) in a subject, said method comprising administering to the subject an effective amount of alphaxalone, alphadolone and/or alphadolone acetate or a pharmaceutically acceptable salt of any one or more thereof formulated in a sulfobutyl ether beta-cyclodextrin.

2. The method of claim 1 wherein the alphaxalone, alphadolone and/or alphadolone acetate does not induce substantive apoptosis of neurones or glial cells.

3. The method of claim 1 wherein prolonged use of the alphaxalone, alphadolone and/or alphadolone acetate does not cause neurocognitive impairment in human subjects.

4. The method of claim 1 wherein the neuroinflammatory-promoting condition is an infection or a neurodegenerative condition.

5. The method of claim 1 wherein the sulfobutyl ether beta-cyclodextrin is (7) sulfobutyl ether beta-cyclodextrin.

6. The method of claim 5 wherein the molar ratio of alphaxalone, alphadolone and/or alphadolone acetate to cyclodextrin is from about 1:1 to 1:6 except for alphadolone wherein the molar ratio is from 1:2 to 1:6.

7. The method of claim 6 wherein the molar ratio of alphaxalone, alphadolone and/or alphadolone acetate to cyclodextrin is from about 1:2 to about 1:4.

8. The method of claim 7 wherein the molar ratio of alphaxalone, alphadolone and/or alphadolone acetate to cyclodextrin is about 1:2.

9. The method of claim 1 further comprising one or more of an antimicrobial agent, a preservative, a buffer and/or a co-polymer.

10. The method of claim 9 wherein the co-polymer is selected from hydroxy propyl methyl cellulose, polyvinyl pyrollidone and carboxymethyl cellulose.

11. The method of claim 9 wherein if a buffer is present, the pH is from about pH 5.5 to about pH 8.

12. The method of claim 1 wherein alphaxalone and/or alphadolone and/or alphadolone acetate is/are used at anaesthetic concentration of 0.25 mg/kg to 100 mg/kg body weight.

13. The method of claim 1 wherein alphaxalone is used at a sedating concentration of 0.05 mg/kg to 10 mg/kg body weight.

14. The method of claim 4 where the neurodegenerative condition is selected from the group consisting of Alzheimer's disease, Parkinson's disease, dementia, stroke, Huntington's disease and traumatic brain injury.

15. The method of claim 4 wherein the infection is herpes, AIDS or meningitis.

* * * * *